United States Patent [19]

Simpson et al.

[11] Patent Number: 5,664,521
[45] Date of Patent: Sep. 9, 1997

[54] APPARATUS FOR AND METHOD OF MILKING AN ANIMAL

[75] Inventors: Sydney William Simpson, Oswestry; Alan Clare, Warrington, both of United Kingdom

[73] Assignee: Tickleford Limited, Douglas, United Kingdom

[21] Appl. No.: 244,708

[22] PCT Filed: Oct. 9, 1992

[86] PCT No.: PCT/GB92/01848

§ 371 Date: Jun. 6, 1994

§ 102(e) Date: Jun. 6, 1994

[87] PCT Pub. No.: WO94/08450

PCT Pub. Date: Apr. 28, 1994

[51] Int. Cl.⁶ .................................................. A01J 5/007
[52] U.S. Cl. ............................ 119/14.02; 119/14.08; 119/14.55
[58] Field of Search ................. 119/14.02, 14.08, 119/14.14, 14.54, 14.55

[56] References Cited

U.S. PATENT DOCUMENTS

| 4,190,020 | 2/1980 | Tamás et al. | 119/14.08 |
| 5,052,341 | 10/1991 | Woolford et al. | 119/14.2 |

FOREIGN PATENT DOCUMENTS

| 0018419 | 2/1980 | European Pat. Off. | |
| 293429 | 8/1991 | Germany | 119/14.08 |
| 389759 | 11/1973 | U.S.S.R. | 119/14.55 |
| 1314326 | 4/1973 | United Kingdom | |
| 1314327 | 4/1973 | United Kingdom | |
| 1494831 | 12/1977 | United Kingdom | |
| 1525741 | 9/1978 | United Kingdom | |
| 2055543 | 3/1981 | United Kingdom | |

OTHER PUBLICATIONS

New Zealand Patent Office Journal, No. 1359, vol. 18, Issue No. 7, dated Aug. 26, 1992, relating to New Zealand Patent 233,620.

Onyango et al, "A Low Maintenance Conductivity Sensor for Detecting mastitis," Journal of Agricultural Engineering Research (1988) 40, pp. 215–216.

Lake et al, "Trials of a novel mastitis sensor on experimentally infected cows," Journal of Dairy Research (1992) pp. 1 and 2.

Primary Examiner—Robert P. Swiatek
Attorney, Agent, or Firm—William R. Hinds

[57] ABSTRACT

Transducers 114 are acted upon by milk flowing respectively from each teat of the animal into a milking claw which has an upper chamber 119 and a lower chamber 120. The transducers respond to a condition of the milk and control valves 128. If the transducer indicates normal milk, valve 128 is set to direct flow into the lower chamber 120 from which it passes via pipe 122 to a collection tank. If abnormal milk is indicated, valve 128 is set to direct flow into the upper chamber 119, from which it passes via pipe 124 to a dump bucket or drain.

16 Claims, 6 Drawing Sheets

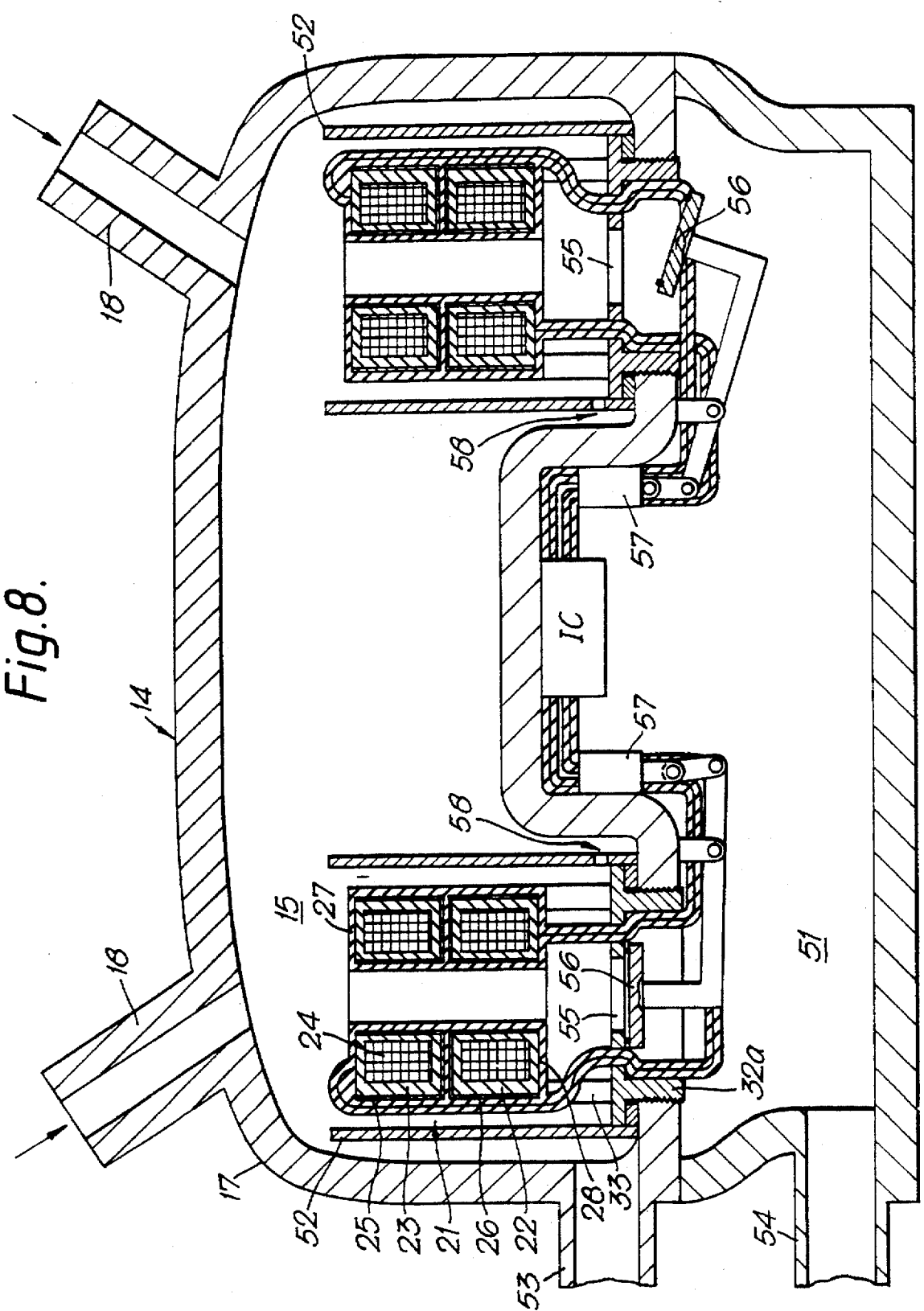

APPARATUS FOR AND METHOD OF MILKING AN ANIMAL

The invention relates to apparatus for and a method of milking an animal and is concerned with the automatic provision of information about the animal during milking by monitoring the milk and detecting a monitored condition in the milk, if such condition arises.

An electrical measuring device is known from German patent specification DE 1949559 for examination of milk during milking for pathological-changes, in particular changes indicative of mastitis infection. Measuring transducers, responding to the conductivity and/or permeability and/or the dielectric constants of the milk, are arranged to monitor milk originating from different teats of the animal being milked.

One problem is the provision of a reference standard because the mentioned properties of the milk, even when normal, will vary from one animal to another, from one day to another and in dependence upon the food the animal has been eating. The solution proposed by DE 1949559 relies upon the observation that it is common for mastitis to affect, at least initially, only one of the four teats of the udder. Accordingly DE 1949559 arranges the four transducers in a bridge circuit, which goes unbalanced if the conductivity of the milk from one teat changes with respect to that from the other three teats. There is, however, no indication of which teat is the source of milk of changed conductivity.

An appreciation on which the present invention is based, is the concept of rapid automatic indication of which path is carrying milk from an infected teat, and further, providing automatic control to divert the outflow of such milk when detected. For realisation of these concepts new solutions have been devised for the provision of both a reference standard and adequate detection sensitivity.

In accordance with the present invention, in one of its aspects, there is provided apparatus for use in the milking of an animal which comprises a plurality of inlet paths and a common outlet path, a respective transducer associated with each inlet path for providing a quantitative signal representing the magnitude of a property of milk in that path, comparison means for comparing the said signal in each inlet path with a reference, characterised in that the comparison means provides an output signal which identifies the inlet path in which the milk has a magnitude of the said property differing by more than a pre-determined amount from the reference magnitude.

For automatic control of the outflow of milk in response to such comparison, a subsidiary outlet path is provided, and each of the said inlet paths is provided with a valve capable of diverting flow from the inlet path away from the said common outlet path to the subsidiary outlet path. Preferably control means responsive to the said output signal actuate the valve in the input path identified by the output signal to divert flow to the said subsidiary outlet path. Conveniently, the control means is so arranged that, during an initial stage of milking, the valves direct milk from all the inlet paths to the subsidiary outlet path and, at the end of the initial stage, some or all of the valves are operated to direct milk from the corresponding inlet paths to the said common outlet path.

The said reference is preferably generated by reference means as an average of the signals representing the respective magnitudes of the property of the milk in the inlet paths. The monitored condition may be the presence in the milk of a substance which is one of the group comprising progesterone, pheromone and substances resulting from the occurrence of mastitis in the animal or an abnormal concentration of such substance in the milk. The monitored property may be electrical conductivity or some other property of the milk and the indication may be provided when the value of the property falls below or exceeds a threshold value.

The milk may be monitored by determining the effect of the milk on energy applied to the milk. The energy may be electromagnetic energy, alternatively, the milk may be monitored by monitoring the value of an electrical property of a device which is exposed to the milk or to substances from the milk.

The milk may be monitored by means of a known technique for detecting the presence of specific, organic substances.

Preferably, the milk is monitored continually during at least a substantial part of the milking process.

Preferably at least one of the transducers is a non-intrusive transducer and preferably the or each transducer comprises a plurality of electromagnetic inductors arranged to be electromagnetically coupled by milk in the corresponding inlet path.

In one arrangement according to the invention the or each transducer comprises a pair of toroidally wound coils arranged so that the milk forms an electrically conducting loop threading the toroids formed by the toroidally wound coils. To minimise coupling between the respective coils other than that provided by the milk, the coils are contained in, but electrically insulated from, appropriately toroidally shaped containers made from electrically conducting material, preferably copper. The containers are open at one end in a plane parallel with the plane containing the continuous axis of the toroid. It is convenient to mount each pair of containers adjacent, but electrically insulated from, one another on the same major axis but back to back, that is with their respective open ends remote from one another.

With such an arrangement, measurement may be carried out by connecting an electrical power supply to provide an alternating current drive to the drive coil and connecting an electrical signal detection circuit to detect the amplitude of the alternating current induced in the detection coil.

According to a further aspect of the invention each coil is a component of a resonant circuit and the said detection circuit is connected to control the power supply so as to maintain the frequency of the alternating current drive to the drive coil at or close to the resonant frequency of the circuit containing the detection coil.

The invention also provides a method of milking an animal wherein milk from respective teats of the animal is monitored and, if no abnormal condition is detected, then milk from all teats of the animal is directed along a common, main path and, if an abnormal condition in the milk from a teat is detected, milk from that teat is directed along a subsidiary path whilst milk from the other teats is directed along the common, main path.

Preferably milk is drawn concurrently from a plurality of teats of the animal, a property of milk drawn from each teat is compared during milking with the same property of milk drawn from each other teat and, whilst said property has substantially the same value for all of the teats, the milk drawn from all of the teats is directed along a common discharge path and, if the value of said property of the milk from one teat departs substantially from the value of said property of the milk from the other teat or teats, the milk from either the one teat or the other teat or teats is diverted from the common discharge path.

Once the milk from one teat or from the other teat or teats has been diverted from the common discharge path, it is preferred that diversion of the milk from that teat or from the other teat or teats from the common discharge path is maintained, irrespective of whether the value of said property of the milk from the one teat reverts to a value substantially the same as the value of that property of the milk from the other teat or teats.

Specific constructions of apparatus and methods embodying the invention will now be described by way of example and with reference to the drawings filed herewith, wherein.

Figure 3:
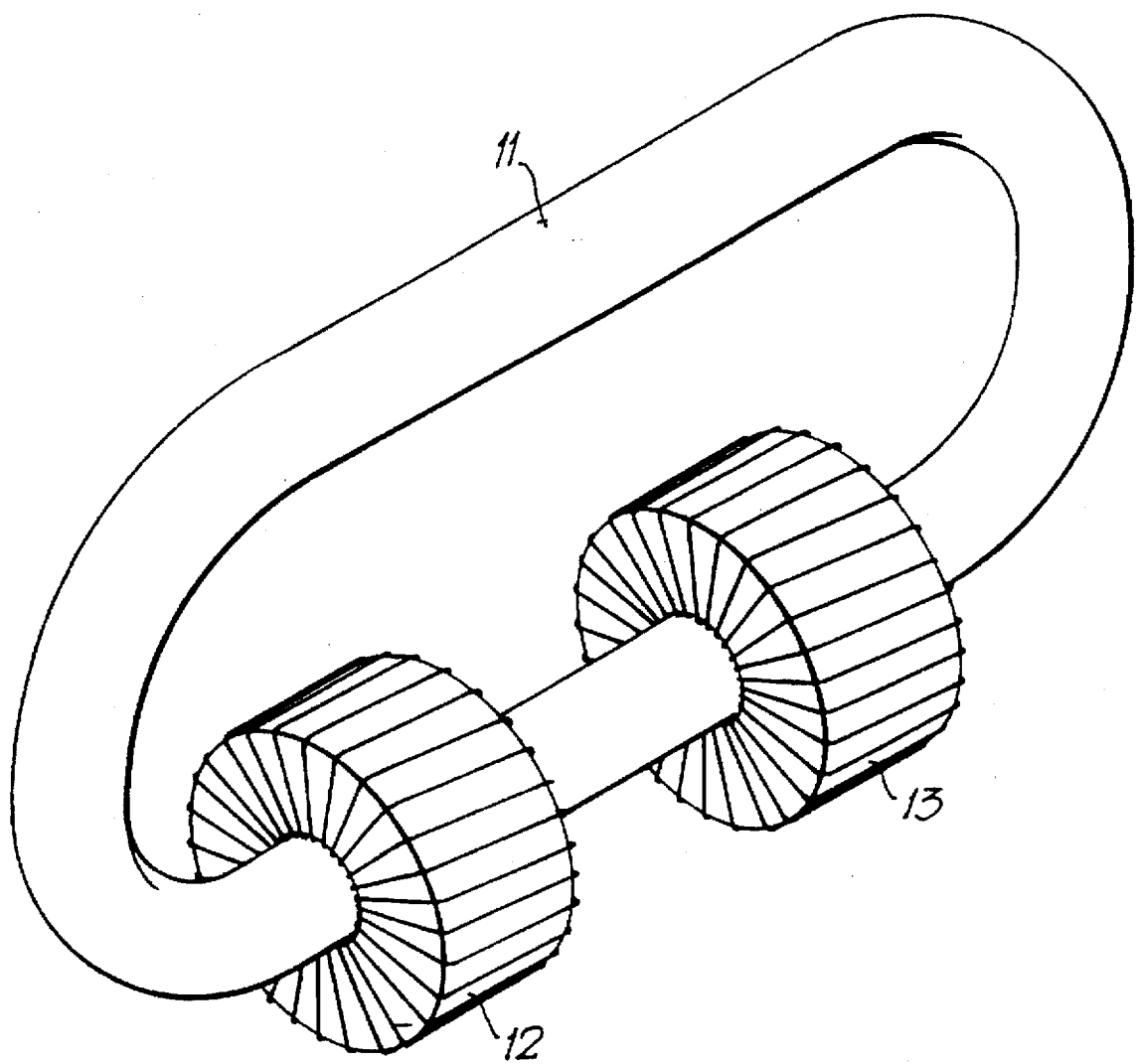
Figure 3A:
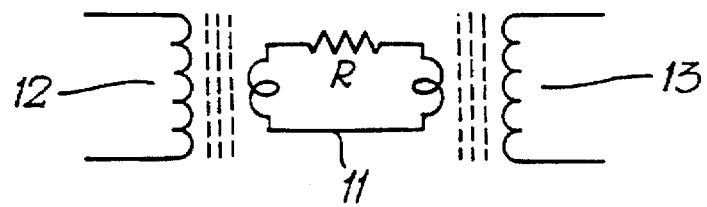
Figure 4:
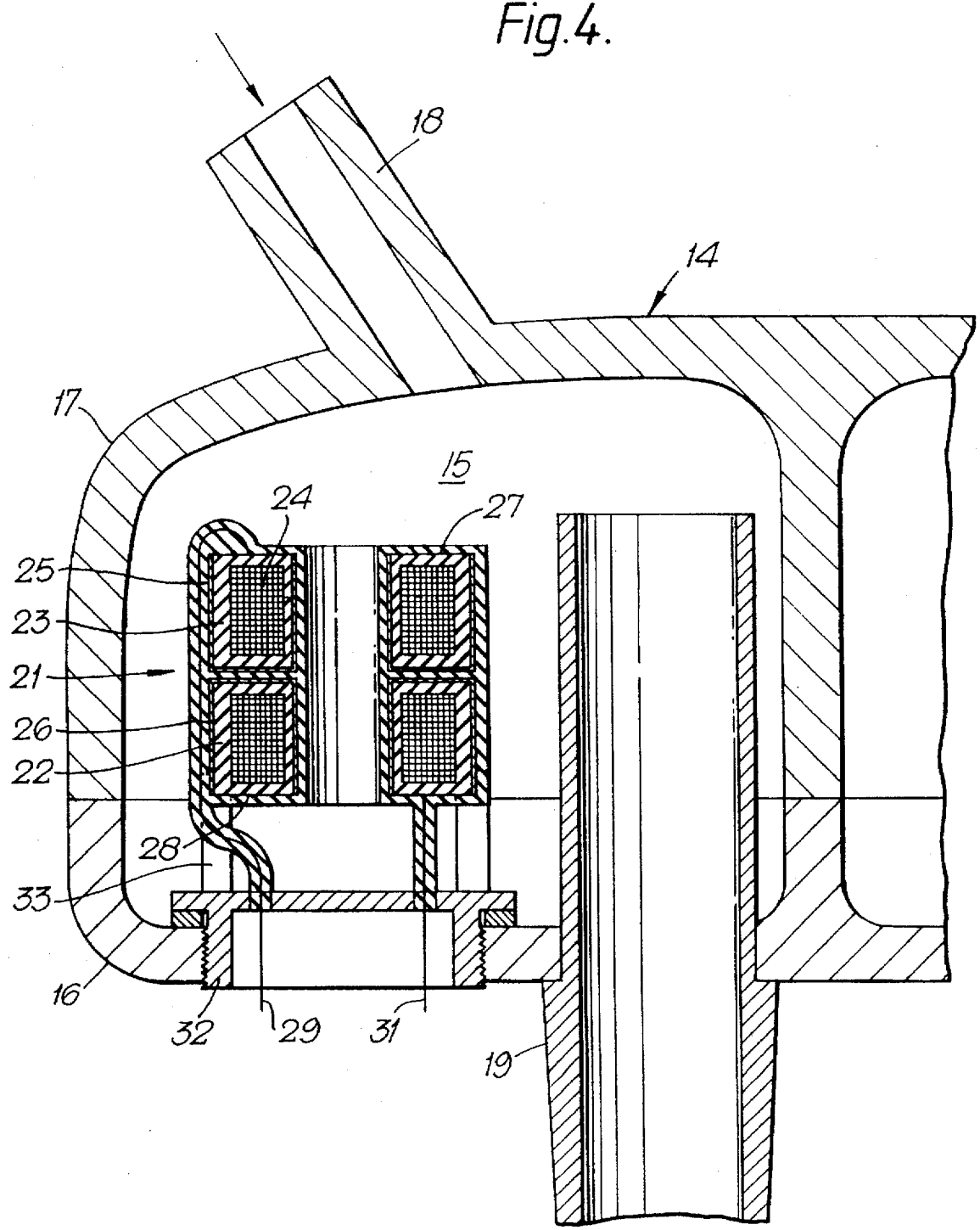
Figure 5:
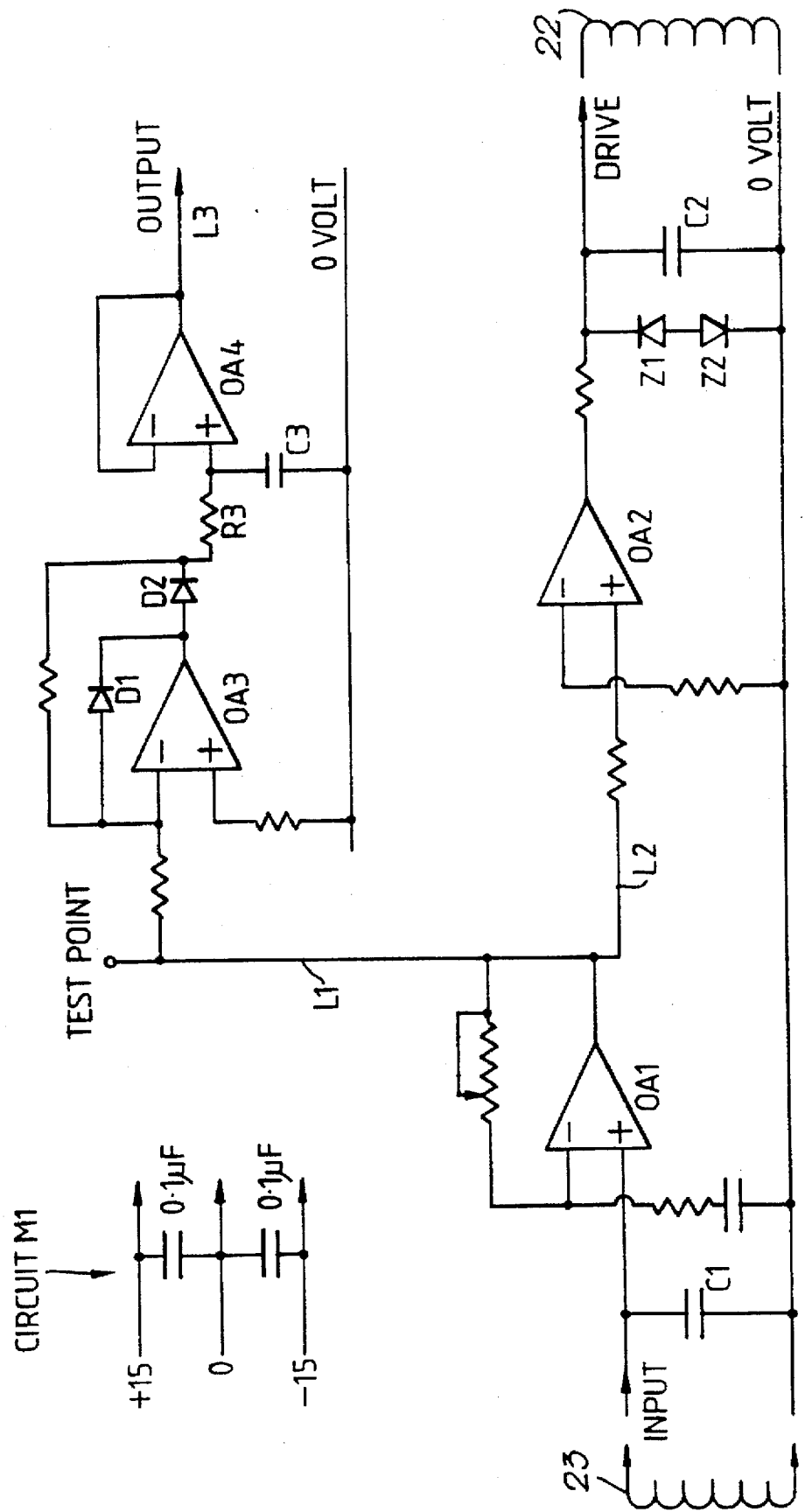
Figure 6:
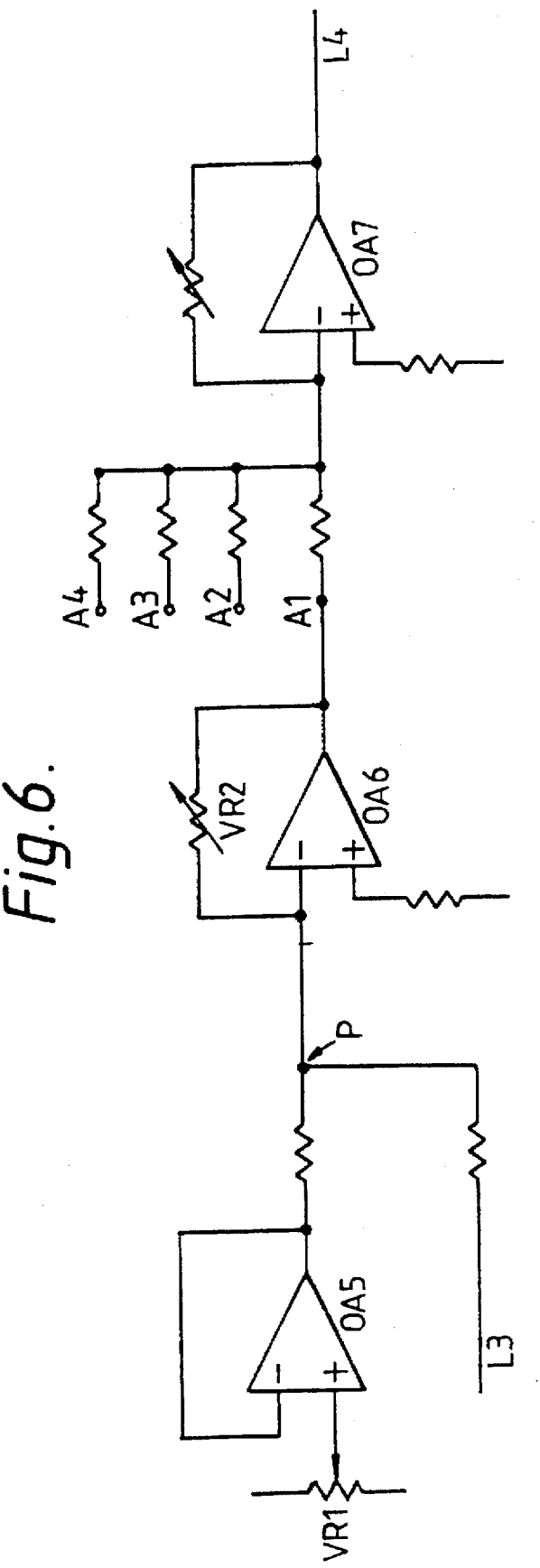
Figure 7:
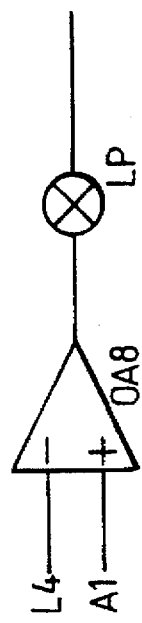

FIG. 3 is a diagrammatic representation of a known arrangement for illustrating the principle of operation of an electrical detection apparatus, FIG. 3a is a representation of the equivalent electrical circuit of FIG. 3, FIG. 4 is a part sectional view of another milking claw containing an electrical detection apparatus, FIG. 5 is a circuit diagram of part of the electronic circuitry of the apparatus, FIG. 6 is a circuit diagram of another part of the electronic circuitry, FIG. 7 is a circuit diagram of a further part of the electronic circuitry, FIG. 8 is a part-sectional diagrammatic representation of a modification of the milking claw of FIG. 4.

Figure 1:
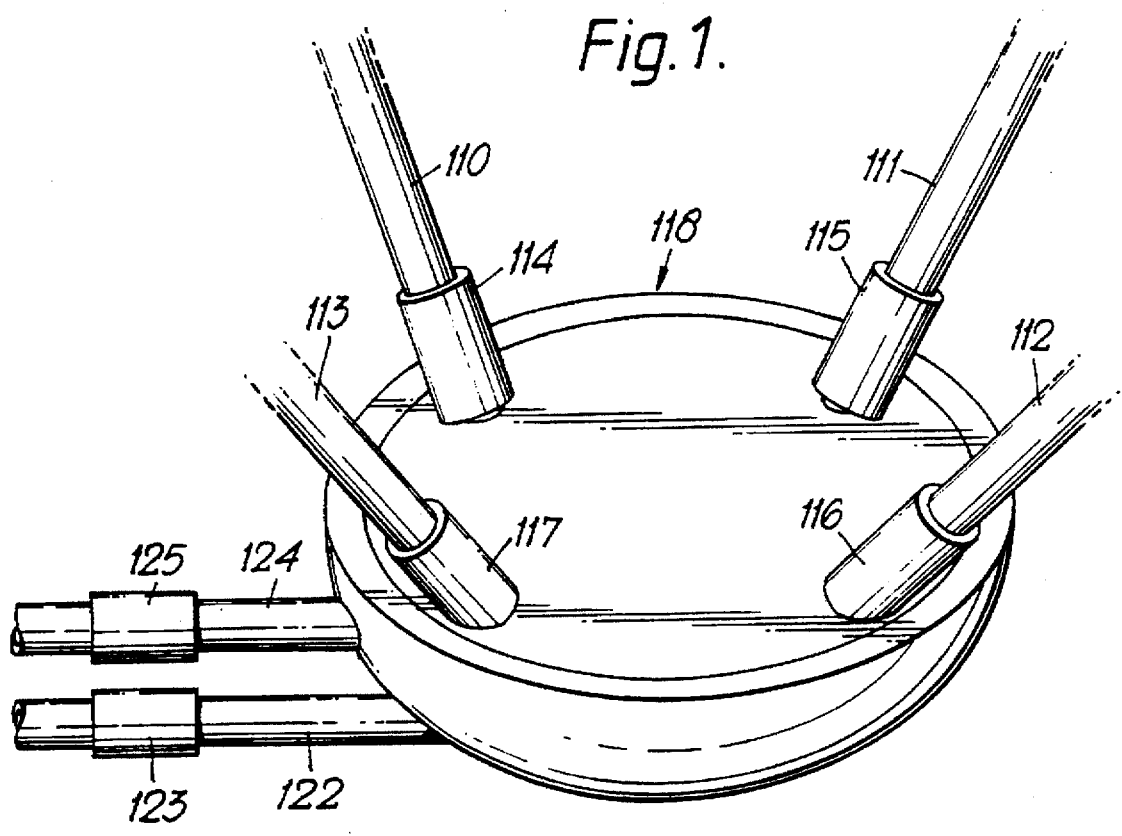
FIG. 1 is a perspective view of a milking claw.

FIG. 1 shows that part of a milking machine which is referred to as the "claw" and is suitable for use in the milking of a cow having an udder with four teats. The claw has tubes 110 to 113 which lead to known teat cups (not shown) which are applied to the teats of a cow for milking. The tubes 110 to 113 lead via respective transducers 114 to 117 to a hollow housing 118 which is divided into upper and lower chambers 119 and 120 by a partition 121.

A main pipe 122 leads from the chamber 120, via a transducer 123, to a milk treatment device, for example a cooler, and a milk storage tank. A pipe 124 leads from the chamber 119 via a transducer 125 to a dump bucket (not shown) or a drain. Pulse tubes are omitted from the drawing for clarity but may be arranged in known manner.

Figure 2:
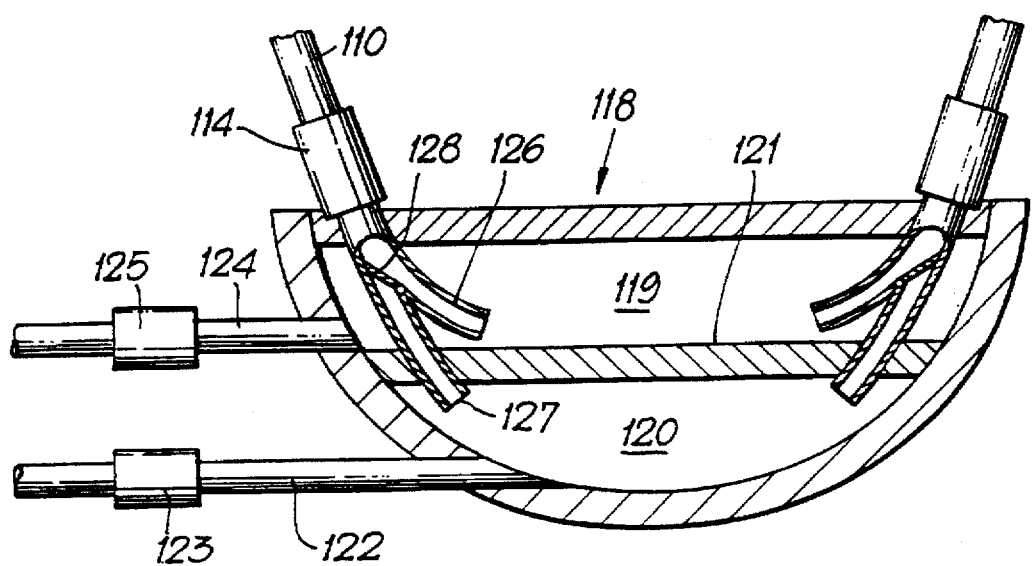
FIG. 2 is a cross-section through the claw of FIG. 1.

Inside the housing 118, the tube 110 divides into branches 126 and 127 which lead respectively into the chambers 119 and 120. A valve 128 represented diagrammatically in FIG. 2 is provided to direct milk entering the housing 118 along the tube 110 into either the branch 126 or the branch 127. An electrically energisable actuator (not shown) is provided for moving the valve 128 to a selected position. Each of the tubes 111, 112 and 113 is provided with branches corresponding to the branches 126 and 127 and with a valve corresponding to the valve 128.

The transducer 114 is adapted for applying energy to the milk and means is provided for monitoring the effect of the milk on the applied energy. The transducer 114 may be a known device for applying electromagnetic energy to the milk which flows along the tube 110 and known means for responding to the effect of the milk on the applied energy. The operation of the transducer 114 may be based on a known technique for detecting the presence of specific, organic substances. The transducer 114 may be other than a transducer for applying energy to the milk. The transducer 114 may be an electrical device, a property of which is affected by one or more specific substances which may be present in the milk. For example, the device may be an ion sensitive field effect transistor. Alternatively, the device may be arranged for carrying out chromatographic analysis of the milk. The passage for flow of milk past the transducer may be arranged to exclude air bubbles from a part of the passage in the vicinity of the transducer.

The transducers 115, 116 and 117 may be identical with the transducer 114. The transducers 123 and 125 may differ from the transducers 114 to 117 but each may be one of the kinds of devices mentioned above. The transducers 123 and 125 may be adapted for determining the presence of one or more specific substances whilst the transducers 114 to 117 are adapted for detecting the presence of one or more different substances. However, in an arrangement in which each of the transducers 114 to 117 is capable of detecting the presence of each substance which is to be monitored in the milk, then the transducers 123 and 125 may be omitted.

The transducers 114 to 117, 123 and 125, or some of these transducers, are connected with a processor (not shown) for processing signals provided by the transducers. The processor may be incorporated in the housing 118 or may be at a central station remote from the housing. In the latter case, the processor is preferably arranged to process signals received from a number of claws identical to or similar to the claw of FIGS. 1 and 2. The central station may include one or more indicators, for example a device providing a visual indication of an abnormal or seasoned condition, and preferably includes means for recording information derived from the several claws.

In one example of a method embodying the present invention, the apparatus of FIGS. 1 and 2 is used in the milking of a cow. Initially, the valves are set to divert milk from each teat into the chamber 119, during an initial stage of milking, which may last for only a few seconds, the fore milk is discarded. Also, during this initial stage of milking, the milk from each teat is monitored by the transducers 114 to 117 for the presence of substances which are produced by mastitis in the udder of the cow. If no such substances are detected, then, after the initial stage of milking, the valves are operated to divert the milk from all of the teats into the chamber 120, from which it flows to the storage tank.

If, during the initial stage of milking, the presence in the milk from one teat of a substance which results from mastitis of the udder is detected, then the milk from that teat is not diverted to the chamber 120, but continues to flow to the chamber 119, from which it is discarded. Milk which is contaminated by the occurrence of mastitis in the cow is thus prevented from reaching the chamber 120 and the milk storage tank.

In this example, the monitoring is carried out only during the initial stage of milking and the valves then set, according to the result, for the duration of the milking of the particular animal on that occasion. Whilst it is possible for the apparatus to be set to continue to monitor for the duration of the milking process, this has been found to be unsatisfactory in that milk ceases to flow at different times from different teats. As the flow from one teat diminishes, air entering the milk in the region of the transducer will change the output and may lead to a false indication.

One property of milk which is affected by the presence of a substance resulting from mastitis is the electrical conductivity. Thus, in a particular example, the transducers 114 to 117 may be transducers which provide an electrical signal which represents the electrical conductivity of the milk. The signals from the transducers 114 to 117 can be compared electronically to provide a comparison of the electrical conductivity of the milk from each teat. An output from the electronic comparison can be used to provide automatic control of actuation of the valves 128.

Additionally, manually operable or remotely operable means may be provided for controlling actuation of the valves 128 and this may over-ride automatic control. Provision is made for resetting the valves after manual operation.

In another embodiment, the transducers 114 to 117 may be adapted to provide signals representing the concentration of ions, for example potassium ions, sodium ions or hydrogen ions, or to provide a signal indicating the concentration of nagase in the milk.

In another embodiment transducers 114 to 117 are adapted for providing signals which indicate the presence of or the concentrations of other substances in the milk, for example progesterone and pheromone. The presence of these substances in the milk provides an important indication about the condition of the cow and comparison of the concentrations in the milk from different teats may not provide additional useful information. Thus, such a transducer provided at 123 or 125 could be used to obtain this information.

FIGS. 3 to 7 illustrate an apparatus embodying the invention in which electrical conductivity of milk is monitored so as to provide an indication of the presence of a substance resulting from mastitis.

FIG. 3 illustrates the known principle upon which the electrical detection apparatus of this example is based. Two toroidally wound coils comprise windings on a former which may best be visualised as a rectangular section straight rod on which windings extend from one end to the other, and the rod is then bent so that its ends join and its axis (the continuous axis) forms a circle. A medium 11, whose electrical conductivity is to be measured, is arranged to form a conductive loop threading the two coils which provide respectively a drive coil 12 and a detection coil 13.

If the drive coil 12 is excited with an alternating electrical current, the conducting loop 11 of the test medium will provide coupling by transformer action with the detection coil 13. The degree of coupling between the drive coil 12 and the detection coil 13 is dependent upon the conductivity of the conducting loop 11. A measure of this conductivity can thus be derived from measurement of the current induced in the detection coil 13.

Whilst, in principle, the magnetic field produced by toroidally wound coils is wholly contained within the toroid, precautions must be taken to ensure that there is no coupling, or substantially no coupling between the drive coil and the detection coil except that provided via the loop of conductive medium 11.

FIG. 3a represents schematically the equivalent circuit of FIG. 3.

FIG. 4 shows the electrical detection apparatus incorporated in a milking claw which comprises an enclosure 14 which is generally circular in plan and divided into four quadrants to provide four independent chambers 15, one of which is shown fully in section in FIG. 4. The enclosure 14 is formed from two separable components, a base plate 16 and a cap 17.

Each of the four chambers 15 has an inlet pipe 18 and a removable outlet pipe 19 for connection respectively to a tube which leads to a known teat cup (not shown) to be applied to the teat of a cow for milking and, on the outlet side, to a tube leading to the milk collection tank.

Screw threaded into a hole in the base plate 16 in each chamber 15 is a sensor 21 for detecting changes in the electrical conductivity of milk flowing through a chamber 15. The sensor 21 comprises a toroidally wound drive coil 22 and a substantially identically constructed detector coil 23. The coils are wound on rectangular section formers 24 and the windings extend around the full circumferential extent of the toroids. The coil windings are encapsulated in insulating material and fit within appropriately toroidally shaped hollow copper cans 25, 26 which are electrically connected to earth. The drive coil 22 is thus isolated from the detector coil 23. Each can has an open end 27, 28 and the cans 25, 26 are assembled back-to-back so that the open ends 27 and 28 are remote from one another. In this example the copper cans 25 and 26 are spaced apart from one another and the whole assembly encapsulated in insulating material.

Electrical leads 29, 31 to the coils pass through sealed apertures in mounting boss 32.

In the operating position, the access opening of pipe 19 within the chamber 15 is above the level of the top of the sensor 21 so that when milk is flowing through the chamber 15, the sensor 21 will be completely submerged. The encapsulated coils are attached to the mounting boss 32 on legs 33 so that there is space for the milk to form a closed electrically conducting loop which threads both of the toroidally wound coils 22, 23.

The principle of operation of the sensor is as described with reference to FIGS. 3 and 3a. The construction employing the copper cans and encapsulating insulation provides for minimum direct coupling between the drive coil 22 and the detection coil 23.

The electronic components and circuits for driving the sensor 21 and detecting the output signals are illustrated in FIGS. 5 to 7.

Referring to FIG. 5, output from the detection coil 23 is connected across a tuning capacitor C1 to an operational amplifier OA1 providing a gain of approximately 100. Output from the operational amplifier OA1 is fed on line L1 to detection circuitry described further below, and on line L2 to a circuit which controls the drive to the drive coil 22.

All of the operational amplifiers shown in FIGS. 5 to 7 are provided, in conventional manner, with connections to a positive supply and a negative supply. These connections have been omitted from the diagrams to avoid unnecessary complication. However, in FIG. 5 an inset labelled circuit M1 illustrates the supply lines which, in this example, are provided at +15 and −15 volts relative to the ground line. As indicated, it may be desirable to include smoothing capacitors in the supply circuit. It will thus be appreciated that the operational amplifiers are capable of providing an output which can vary between −15 volts and +15 volts relative to the ground line.

The signal on line L2 is applied to operational amplifier OA2 set up as a high gain amplifier operating effectively as a switch. The output from operational amplifier OA2 is applied across Zener diodes Z1 and Z2 connected back-to-back. The drive coil 22 together with its parallel connected tuning capacitor C2 is connected across the back-to-back Zener diodes Z1 and Z2.

When switched on, any initial signal detected from the detection coil 23 will be at the resonant frequency of this coil together with capacitor C1. Consequently the signal on line L2 will cause amplifier OA2 to switch at this frequency. The Zener diodes Z1 and Z2 are therefore driven alternately to breakdown and the output applied across the drive coil 22 is a square wave of amplitude equal to twice the breakdown voltage of the Zener diodes and frequency equal to the resonant frequency of the detection coil 23. This circuit arrangement thus provides that the frequency of the drive is held locked to the resonant frequency of the tuned circuit formed by the detection coil 23 together with the tuning capacitor C1 and will follow changes should there be any as a consequence of changes in the operating conditions of the sensor 21.

The voltage of the output signal from the detection coil 23 is dependent upon the coupling between the drive coil 22 and detection coil 23 which is in turn dependent upon the conductivity of the milk. The output voltage from the detection coil 23 thus provides an indication of conductivity. The sensitivity of this indication is at a maximum when the detection coil 23 is operating at resonance. However, when operating in this way at resonance, any slight departure from the resonant frequency will affect significantly the output voltage. It is thus of critical importance that the frequency of the drive is held at the resonance frequency of the detection coil circuit. In this context, it is preferable for the resonant frequency of the resonant circuit formed by the drive coil 22 and tuning capacitor C2 to match that of the detection coil 23 and tuning capacitor C1. However, this is not critical since the resonant frequency of the drive coil circuit affects the efficiency with which the drive signal is coupled but will not affect the frequency of the drive signal.

Turning now to the detection circuitry, the signal on line L1 is converted to a direct voltage, indicative of the conductivity of the milk, by a half wave rectifier comprising operational amplifier OA3 and associated diodes D1 and D2, the direct negative feedback via diode D1 effectively cutting off the negative half cycle.

The rectified signal is smoothed by the combination of resistor R3 and capacitor C3 and the output buffered by operational amplifier OA4. FIG. 6 shows the continuation of the circuit, with this output on line L3 being combined at a summing point P with a voltage from operational amplifier OA5, the value of which is adjustable by variable resistor VR1 as a zero offset. A further operational amplifier OA6 with variable resistor VR2 in the feedback path provides for scale adjustment and final output from sensor 21 at point A1.

Each sensor in each of the quadrants of the claw 14 is provided with identical electronic circuitry from detection coil to output A1. The corresponding outputs are shown on FIG. 6 labelled A2, A3, A4. These are summed and an average generated by operational amplifier OA7 to provide a reference output on line L4.

For each channel, a comparator OA8, as shown in FIG. 7, is provided and the reference level on L4 compared with the output, shown for A1 in FIG. 7. The comparator OA8 is set up so that lamp LP is illuminated when the signal on Line A1 differs by more than a predetermined amount from the level on line L4.

For operation, the apparatus is initially set up with a liquid in each of the chambers 15 having an electrical conductivity less than is likely to be encountered in the test medium (milk). In each channel, variable resistor VR1 is adjusted to give a scale zero readout. The liquid in each channel is then replaced with a liquid having a conductivity in excess of the maximum expected. In each channel the variable resistor VR2 is adjusted to give a maximum scale deflection. After cleaning, the apparatus is then ready for operation on milk. The reference level on L4 will represent the average conductivity of the milk passing through the four chambers 15. If any one chamber 15 receives milk at a conductivity level differing significantly from the average, then the appropriate lamp LP(5) for that channel will light up.

It will be appreciated that alternatively, or additionally, an output from comparator OA8 may be used to drive a control valve in the outlet pipe 19 to divert milk away from them in collection tank in the event that the sensor in that chamber is indicating a level of conductivity differing from the average by more than a pre-determined amount.

FIG. 8 illustrates in diagrammatic form a modification of the arrangement shown in FIG. 4. Those components which are the same as those shown in FIG. 4 carry the same reference numerals. The section has been extended to show two of the four sensors 21 and two of the inlet pipes 18.

In this modification, the claw has an upper chamber 15 and a lower chamber 51. The upper chamber is not divided into separate quadrants, but each sensor 21 is positioned within a cylindrical pot 52. Each inlet pipe 18 is positioned so as to be directly over the respective pot 52. An outlet pipe 53 leads from the upper chamber 15 to a dump bucket or drain. The lower chamber 51 has an outlet pipe 54 leading to the milk treatment device and milk storage tank.

The support boss 32a of each transducer in this modification has a central aperture 55 providing an outlet opening at the bottom of the respective pot 52. A valve 56 operated by a solenoid 57 is moveable by the solenoid 57 between a closed position and an open position. In FIG. 8, the valve 56 associated with the sensor 21 on the left of the figure is shown in the closed position, whilst the valve on the right hand side of the figure is shown in the open position.

The solenoids 57 and also the integrated circuit electronics package marked IC are accommodated within a recess in the upper part of the chamber 51.

In operation of this modified apparatus, the valves 56 are all initially closed and the first milk to arrive through each of the inlet pipes 18 flows into and fills to overflowing the pots 52 containing the sensors 21. Overflow milk escapes through the outlet pipe 53.

Conductivity measurement on the milk filling each pot 52 at this stage is carried out as described above with reference to FIGS. 4, 5, 6 and 7. If the measurement for any pot 52 indicates mastitis infection, then the valve 56 for that particular pot is held closed for the duration of that milking session. All the milk from the associated teat is thus directed to the dump bucket or drain via pipe 53. When the flow from inlet pipe 18 from that particular teat ceases, remaining milk in the pot 52 drains slowly out through a small drain hole 58 at the bottom of the pot 52.

Where the test on the initial flow of milk into pot 52 shows normal, the valve 56 is opened after the initial short period of time necessary for the test, and the good milk flows into the lower chamber 51 and out to the cooler and collection tank via pipe 54.

On completion of milking, all valves 56 are opened and cleaning is carried out by backwashing via pipe 54.

The representation of the integrated circuits IC and the solenoids 57 and associated linkages are highly diagrammatic. It will be appreciated that any suitable form of valve controlling outflow from the pots 52 into the lower chamber 51 may be used. In particular, it is desirable to employ a valve which can be opened wide to provide a clear and smooth flow path for both the milk flow and, after milking, for the backflow washing.

The invention is not restricted to the details of the foregoing examples. For instance, it is not essential to use zener diodes 21 and 22 in the drive circuitry shown in FIG. 5. The amplifier OA2, operating at high gain, is effectively switched at the natural resonance frequency of the detector circuit. However, the operation of amplifier OA2 is more satisfactory if the zener diodes are included.

Nor is it essential to provide two separate, grounded copper cans 25, 26. An equivalent and effective unitary structure can be provided by a pair of co-axial cylinders with a dividing wall extending across the space between the cylinders perpendicularly to the axis and mid-way between the ends of the cylinders. The unitary structure can be made from any material of suitably high electrical conductivity.

We claim:

1. Apparatus for use in the milking of an animal which comprises a plurality of inlet paths, a common outlet path, a subsidiary outlet path, a respective transducer associated with each inlet path for providing a quantitative signal representing the magnitude of a property of milk in that path, comparison means for comparing the said signal in each inlet path with a reference, the comparison means providing an output signal which identifies the inlet path in which the milk has a magnitude of the said property differing by more than a predetermined amount from the reference magnitude, and a diverter valve in each of the said inlet paths which diverter valve is operable to divert flow from the inlet path away from the said common outlet path to the said subsidiary outlet path.

2. Apparatus as claimed in claim 1, wherein control means responsive to the said output signal actuate the diverter valve in the input path identified by the output signal to divert flow to the said subsidiary outlet path.

3. Apparatus as claimed in claim 2 wherein the control means operate the diverter valves, during an initial stage of milking to direct milk from all of the inlet paths to the subsidiary outlet path and, at the end of the initial stage operates some or all of the valves to direct milk from the corresponding inlet paths to the said common outlet path.

4. Apparatus as claimed in claim 1, wherein reference means generate the said reference as an average of the signals representing the respective magnitudes of the property of the milk in the inlet paths.

5. Apparatus as claimed in claim 1, wherein at least one of the transducers is a non-intrusive transducer.

6. Apparatus as claimed in claim 5, wherein the or each transducer comprises a plurality of electromagnetic inductors arranged to be electromagnetically coupled by milk in the corresponding inlet path.

7. Apparatus as claimed in claim 6, wherein the or each transducer comprises a pair of toroidally wound coils arranged so that the milk forms an electrically conducting loop threading the toroids formed by the toroidally wound coils.

8. Apparatus as claimed in claim 7, wherein the coils are contained in, but electrically insulated from, appropriately toroidally shaped copper containers open at one end in a plane parallel with the plane containing the continuous axis of the toroid.

9. Apparatus as claimed in claim 8, wherein the copper containers contain respectively a drive coil and a detection coil and are mounted adjacent, but electrically insulated from, one another on the same major axis but with their respective open ends remote from one another.

10. Apparatus as claimed in claim 9, wherein an electrical power supply is connected to provide an alternating current drive to the drive coil and an electrical signal detection circuit is connected to detect the amplitude of the alternating current induced in the detection coil.

11. Apparatus as claimed in claim 10, wherein each coil is a component of a resonant circuit and the detection circuit is connected to control the power supply so as to maintain the frequency of the alternating current drive to the drive coil at or close to the resonant frequency of the circuit containing the detection coil.

12. Apparatus as claimed in claim 1 wherein the magnitude of the reference is derived by reference means during milking from the magnitude of the said property of the milk in said plurality of inlet paths.

13. A method of milking an animal wherein milk is drawn concurrently from a plurality of teats of the animal, a property of milk drawn from each teat is compared during milking with the same property of milk drawn from each other teat, and, whilst said property has substantially the same value for all of the teats, the milk drawn from all of the teats is directed along a common discharge path and, when said comparing step shows that the value of said property of the milk from one teat departs substantially from the value of said property of the milk from the other teat or teats, the milk from either the one teat or the milk from the other teat or teats is diverted from the common discharge path whilst undiverted milk continues to flow along the said common discharge path.

14. A method according to claim 13, wherein, once the milk from the one teat or from the other teat or teats has been diverted from the common discharge path, diversion of the milk from that teat or from the other teat or teats from the common discharge path is maintained, irrespective of whether the value of said property of the milk from the one teat reverts to a value substantially the same as the value of that property of the milk from the other teat or teats.

15. A method according to claim 13, wherein, during an initial stage of milking, milk from all of the teats is directed to a common, subsidiary discharge path, irrespective of the values of said property of the milk from the several teats and, at the end of the initial stage of milking, the milk from all of the teats is directed to a common main discharge path, unless the value of said property of the milk from one teat departs substantially from the value of said property of the milk from the other teat or teats, in which case milk from the one teat continues to be directed to the subsidiary discharge path.

16. A method of milking an animal wherein milk is drawn concurrently from a plurality of teats of the animal, a property of milk drawn from each teat is compared with a reference magnitude of said property, which reference magnitude is derived during milking from the magnitude of the said property of the milk drawn from the said plurality of teats, and, when said comparing step shows that the magnitude of said property of the milk from any one of the teats differs by more than a predetermined amount from the reference magnitude, the milk from the said one teat or the milk from the other teat or teats is diverted from the common discharge path, whilst undiverted milk continues to flow along the said common discharge path.

* * * * *